(12) United States Patent
Nie et al.

(10) Patent No.: US 7,648,845 B2
(45) Date of Patent: *Jan. 19, 2010

(54) POROUS MATERIALS EMBEDDED WITH NANOSPECIES, METHODS OF FABRICATION THEREOF, AND METHODS OF USE THEREOF

(75) Inventors: Shuming Nie, Atlanta, GA (US); Xiaohu Gao, Decatur, GA (US)

(73) Assignee: Emory University, Atlanta, GA (US)

( * ) Notice: Subject to any disclaimer, the term of this patent is extended or adjusted under 35 U.S.C. 154(b) by 339 days.

This patent is subject to a terminal disclaimer.

(21) Appl. No.: 11/385,504

(22) Filed: Mar. 20, 2006

(65) Prior Publication Data

US 2009/0169861 A1    Jul. 2, 2009

Related U.S. Application Data

(63) Continuation-in-part of application No. 10/666,587, filed on Sep. 18, 2003, now Pat. No. 7,037,729.

(60) Provisional application No. 60/492,416, filed on Aug. 4, 2003.

(51) Int. Cl.
    *G01N 33/544* (2006.01)
(52) U.S. Cl. .................. 436/535; 436/518; 436/524; 436/525; 436/528; 436/532; 435/287.2
(58) Field of Classification Search .......... 422/50, 422/52, 55, 68.1; 436/518, 524, 525, 528, 436/532, 535; 435/7.1, 283.1, 287.1, 288.1
See application file for complete search history.

(56) References Cited

U.S. PATENT DOCUMENTS

| | | | |
|---|---|---|---|
| 5,120,643 A | 6/1992 | Ching et al. | 435/7.92 |
| 5,268,097 A * | 12/1993 | Girot et al. | 210/198.2 |
| 5,922,537 A | 7/1999 | Ewart et al. | 435/6 |
| 6,103,476 A | 8/2000 | Tyagi et al. | |
| 6,251,303 B1 | 6/2001 | Bawendi et al. | 252/301.4 |
| 6,379,622 B1 | 4/2002 | Polak et al. | 422/82.06 |
| 6,468,808 B1 | 10/2002 | Nie et al. | 436/524 |
| 6,503,831 B2 | 1/2003 | Speakman | 438/674 |
| 6,514,295 B1 | 2/2003 | Chandler et al. | 8/607 |
| 6,524,793 B1 | 2/2003 | Chandler et al. | 435/6 |
| 6,528,323 B1 | 3/2003 | Thayer et al. | 436/518 |

(Continued)

FOREIGN PATENT DOCUMENTS

| | | | | |
|---|---|---|---|---|
| WO | WO 00/55631 A1 | 9/2000 | | 33/58 |
| WO | WO 00/71995 A2 | 11/2000 | | 21/77 |
| WO | WO 03/003015 A2 | 1/2003 | | 33/544 |
| WO | WO 03/003015 A2 | 9/2003 | | |

OTHER PUBLICATIONS

Damle et al. Multilayer Langmuir-Blodgett assemblies of hydrophobized CdS nanoparticles by organization at the air-water interface. 2002. J. Mater. Chem., vol. 10, 1389-1393).*

(Continued)

*Primary Examiner*—Bao-Thuy L Nguyen
*Assistant Examiner*—Melanie J. Yu
(74) *Attorney, Agent, or Firm*—Thomas, Kayden, Horstemeyer & Risley, LLP

(57) ABSTRACT

Briefly described, embodiments of this disclosure include structures, methods of forming the structures, and methods of using the structures. One exemplary structure, among others, includes a nanospecies and a porous material. The nanospecies has a first characteristic and a second detectable characteristic. In addition, a second detectable energy is produced corresponding to the second detectable characteristic upon exposure to a first energy. The porous material has the first characteristic and a plurality of pores. The first characteristic causes the nanospecies to interact with the porous material and become disposed in the pores of the porous material.

25 Claims, 4 Drawing Sheets

U.S. PATENT DOCUMENTS

| | | | |
|---|---|---|---|
| 6,541,203 | B2 | 4/2003 | Mitchison ................... 435/6 |
| 6,544,732 | B1* | 4/2003 | Chee et al. .................. 435/6 |
| 6,567,678 | B1 | 5/2003 | Oosta et al. |
| 6,642,538 | B2 | 11/2003 | Efros et al. .................. 257/30 |
| 6,710,366 | B1 | 3/2004 | Lee et al. |
| 6,783,699 | B2 | 8/2004 | Li et al. |
| 2002/0090650 | A1 | 7/2002 | Empedocles et al. ......... 435/7.1 |
| 2002/0182609 | A1 | 12/2002 | Arcot ........................ 435/6 |
| 2003/0027126 | A1* | 2/2003 | Walt et al. .................. 435/4 |
| 2003/0148544 | A1 | 8/2003 | Nie et al. |

OTHER PUBLICATIONS

C.B. Murray, D.J. Norris, and M.G. Bawendi, "Synthesis and Characterization of Nearly Monodisperse CdE (E=S, Se, Te) Semiconductor Nanocrystallites," Mar. 22, 1993, J. Am. Chem. Soc. vol. 115, pp. 8706-8715.

Lianhua Qu, Z. Adam Peng, and Xiaogang Peng, "Alternative Routes toward High Quality CdSe Nanocrystals," May 15, 2001. Nano Letters, vol. 1, No. 6, pp. 333-337.

Xiaogang Peng, Michael C. Schlamp, Andreas V. Kadavanich, and A.P. Alivisatos, "Epitaxial Growth of Highly Luminescent CdSe/CdS Core/Shell Nanocrystals with Photostability and Electronic Accessibility," Mar. 10, 1997. J. Am. Chem. Soc.

Mingyong Han, Xiaohu Gao, Jack Z. Su, and Shuming Nie, "Quantum-dot-tagged microbeds for multiplexed optical coding of biomolecules," Jul. 2001. pp. 631-635.

Wolfgang J. Parak, Rosanne Boudreau, Mark LeGros, Daniele Gerion, Daniela Zanchet, Christine M. Micheel,, Shara C. Williams, A. Paul Alivisatos, and Carolyn Larabell, "Cell Motility and Metastatic Potential Studies Based on Quantum Dot Imaging of Phagokinetic Tracks," Jun. 18, 2002. Advanced Materials, vol. 14, p. 882.

Mahesh K. Bhalgat, Rosaria P. Haugland, Jeffrey S. Pollack, Sharon Swan, Richard P. Haugland, "Green-and-red-fluorescent nanospheres for the detection of cell surface receptors by flow cytometry," Jun. 21, 1998. Journal of Immunological methods. vol. 219, pp. 37-68.

J. R. Kettman, T. Davies, D. Chadler, K.G. Oliver, and R.J. Fulton, "Classification and Properties of 64 Multiplexed Microsphere Sets," Jun. 10, 1998. Cytometry. pp. 234-243.

R. Jerrold Fulton, Ralph L. McDade, Perry L. Smith, Laura J. Kienker, and John R. Kettman Jr., "Advanced multiplexed analysis with the FlowMetrix™ system," Clinical Chemistry 43:9, 1749-1756 (1997).

Keith J. Albert and David R. Walt, "Optical Multibead Arrays for Simple and Complex Odor Discrimination," Jun. 1, 2001. Anal. Chem. pp. 2501-2508.

Keith J. Albert and David R. Walt, "High-Speed Fluorescence Detection of Explosives-like Vapors," Anal. Chem. 2000, 72, 1947-1955.

Karri, L. Michael, Laura C. Taylor, Sandra L. Schultz, and David R. Walt, "Randomly Ordered Addressable High-Density Optical Sensor Arrays," Anal. Chem. 1998, 70, 1242-1248.

Jane A. Ferguson, Frank J. Steemers, and David R. Walt, "High-Density Fiber-Optic DNA Random Microsphere Array," Anal. Chem. 2000, 72, 5618-5624.

Nikolai Gaponik, Igor L. Radtchenko, Gleb B. Sukhorukov, Horstt Weller, and Andrey L. Rogach, "Toward Encoding Combinatorial Libraries: Charge-Driven Microencapsulation of Semiconductor Nanocrystals Luminescing in the Visible and Near IR," Adv. Mater. 2002, 14 No. 12, Jun. 18.

Kevin Braeckmans, Stefaan C. DeSmedt, Marc Leblans, Rudi Pauwels and Joseph Demeester, "Encoding Microcarriers: Present and Future Technologies," Nature Reviews/Drug Discovery, vol. 1, Jun. 2002. pp. 447-456.

Bronwyn J. Battersby, Gwendolyn A. Lawrie, Angus P.R. Johnston and Matt Trau, "Optical barcoding of colloidal suspensions: applications in genomics, proteomics and drug discovery," Chem Commun., 2002, 1435-1441.

Richard M. Levenson and Clifford C. Hoyt, "Spectral imaging and microscopy," American Laboratory, 2000. pp. 1-8.

J.R. Kettman, T. Davies, D. Chandler, K.G. Oliver, and R.J. Fulton, "Classification and Properties of 64 Multiplexed Microsphere Sets," Cytometry 33:234-243 (1998).

J.W. Kim, J.H. Ryu, K.D. Suh, "Monodisperse micron-sized macroporous poly (styrene-co-divinylbenzene) particles by seeded polymerization," Colloid Polym Sci 279:146-152 (2001).

Q. Ching Wang, Frantisek Svec, and Jean M.J. Frechet, "Fine Control of the Porous Structure and Chromatographic Properties of Monodisperse Macroporous Poly (styrene-co-divinylbenzene) Beads Prepared Using Polymer Porogens," Journal of Polymer Science Part A:Polymer Chemistry, vol. 32, 2577-2588 (1994).

Gregory Bearman, Jet Propulsion Laboratory, California Institute of Technology, Richard Levenson, Cambridge Research and Instrumentation, Woburn, MA, "Biological Imaging Spectroscopy," pp. 1-22. Nov. 26, 2001.

Paul Pantano, Claudia C. Meek, Jing Wang, Decio H. Coutinho and Kenneth J. Balkus, Jr., "Optical encoding with shaped DAM-1 molecular sieve particles," The Royal Society of Chemistry 2003, Lab Chip, 2003, 3, 132-135.

John P. Nolan, Sabine Lauer, Eric R. Prossnitz and Larry A. Sklar, "Flow cytometry: a versatile tool for all phases of drug discovery," Research Focus, DDT vol. 4, No. 4 Apr. 1999. pp. 173-180.

R. Jerrold Fulton, Ralph L. McDade, Perry L. Smith, Laura J. Kienker, and John R. Kettman Jr., "Advanced multiplexed analysis with the FlowMetrix™ system," Clinical Chemistry 43:9, 1749-1756 (1997).

Jan F. Keij and John A. Steinkamp, "Flow Cytometric Characterization and Classification of Multiple Dual-Color Fluorescent Microspheres Using Fluorescence Lifetime," Cytometry 33:318-323 (1998).

Ivan Sondi, Olavi Siiman, Steven Koester, and Egon Matijevic, "Preparation of Aminodextran-CdS Nanoparticle Complexes and Biologically Active Antibody-Aminodextran-CdS Nanoparticle Conjugates," Langmuir 2000, 16, 3107-3118.

Matthew J. Dejneka, Alexander Streltsov, Santona Pal, Anthony G. Frutos, Christy L. Powell, Kevin Yost, Po Ki Yuen, Uwe Muller, and Joydeep Lahiri, "Rare earth-doped glass microbarcodes," PNAS, Jan. 21, 2003, vol. 100, No. 2, 389-393.

Kevin Braeckmans, Stefaan C. DeSmedt, Chris Roelant, Marc Leblans, Rudi Pauwels and Joseph Demeester, "Encoding microcarriers by spatial selective photobleaching," nature materials/VOL 2/ Mar. 2003. pp. 169-173.

John P. Nolan and Larry A. Sklar, "Suspension array technology: evolution of the flat-array paradigm," Trends in Biotechnology, vol. 20, No. 1, Jan. 2002. pp. 9-12.

International Preliminary Examination Report for PCT/US03/29384; International Filing Date Sep. 18, 2003.

Gao, Xiaohu and Shuming Nie., "Doping Mesoporous Materials with Multicolor Quantum Dots", J. Phys. Chem B 2003, 107, 11575-11578.

Scott, Brian J., Wirnsberger Gernot and Stucky Galen D., "Mesoporous and Mesostructured Materials for Optical Applications," Chem. Mater. 20001 13, 3140-3150.

Han, Mingyong, Gao, Xiaohu, Su, Jack Z., and Nie, Shuming, "Quantum-dot-tagged Microbeads for Multiplexed Optical Coding of Biomolecules," http://biotech.nature.com, Jul. 2001, vol. 19, pp. 631-635.

Jakli et al. "Memory of silica aggregates dispersed in smectic liquis crystals: Effect of the interface properties, 1999, The European Physical Journal B, vol. 10, pp. 509-513.

Peng et al. Formation of High-Quality CdTe, CdSe, and CdS Nanocrystals Using CdO as Precursor, Oct. 10, 2000, J. Am. Chem. Soc., vol. 123, pp. 183-184.

Zhang et al. Comparison and Stability of CdSe Nanocrystals Covered with Amphiphilic Poly(Amidoamine) Dendrimers, J. Phys. Chem. B., 2002, vol. 106, pp. 10,316-10,321.

* cited by examiner

POROUS MATERIALS EMBEDDED WITH NANOSPECIES, METHODS OF FABRICATION THEREOF, AND METHODS OF USE THEREOF

CROSS-REFERENCE TO RELATED APPLICATION

This application is a continuation-in-part of application Ser. No. 10/666,587, which is now U.S. Pat. No. 7,037,729, filed Sep. 18, 2003, which claims priority to U.S. provisional application entitled, "POROUS MATERIALS DOPED WITH NANOSPECIES, METHODS OF FABRICATION THEREOF, AND METHODS OF USE THEREOF," having Ser. No. 60/492,416, filed on Aug. 4, 2003, which is entirely incorporated herein by reference.

TECHNICAL FIELD

The present invention is generally related to porous materials and, more particularly, is related to porous materials embedded with nanospecies.

BACKGROUND

Recent advances in bioanalytical sciences and bioengineering have led to the development of DNA chips, miniaturized biosensors, and microfluidic devices. In addition, applications benefiting from fluorescent labeling include medical (and non-medical) fluorescence microscopy, histology, flow cytometry, fundamental cellular and molecular biology protocols, fluorescence in situ hybridization, DNA sequencing, immunoassays, binding assays and separation. These enabling technologies have substantially impacted many areas in biomedical research, such as gene expression profiling, drag discovery, and clinical diagnostics.

Fluorescently-labeled molecules have been used extensively for a wide range of applications. Typically organic dyes are bonded to a probe, which in turn selectively binds to a target molecule. Then the target molecule is identified by exciting the dye molecule, causing it to fluoresce. There are many disadvantages to using an organic dye for these fluorescent-labeling systems. The emission of visible light from an excited dye molecule usually is characterized by the presence of a broad emission spectrum (about 100 nm) and broad tails of emission at red wavelengths (about another 100 nm). As a result, there is a severe limitation on the number of different color organic dye molecules which can be utilized simultaneously or sequentially in an analysis since it is difficult to either simultaneously or even non-simultaneously detect or discriminate between the presence of a number of different detectable substances due to the broad spectrum emissions and emission tails of the labeling molecules.

Another problem is that organic dyes often have a narrow absorption spectrum (about 30-50 nm), thus requiring either multiple wavelength probes, or else a broad spectrum excitation source, which is sequentially used with different filters for sequential excitation of a series of probes respectively excited at different wavelengths. An additional problem associated with organic dyes is their lack of photostability. Often organic dyes bleach or cease to fluoresce under repeated excitation.

Therefore, there is a need in the industry for more accurate, sensitive, and broader method of detection.

SUMMARY OF THE INVENTION

Briefly described, embodiments of this disclosure include structures, methods of forming the structures, and methods of using the structures. One exemplary structure, among others, includes a nanospecies and a porous material. The nanospecies has a first characteristic and a second detectable characteristic. In addition, a second detectable energy is produced corresponding to the second detectable characteristic upon exposure to a first energy. The porous material has the first characteristic and a plurality of pores. The first characteristic causes the nanospecies to interact with the porous material and become disposed in the pores of the porous material.

The structure described above can be used in array systems, flow cytometry systems, diagnostic libraries, combinatorial libraries, fluorescent inks, and fluorescent cosmetics, for example.

Methods of fabricating structures are also provided. One exemplary method includes, among others, the following steps: providing a nanospecies having a first characteristic and a second detectable characteristic, wherein a second detectable energy is produced corresponding to the second detectable characteristic upon exposure to a first energy; providing a porous material having the first characteristic; introducing the nanospecies and the porous material in the presence of a solution; and forming the structure, wherein the structure includes a porous material having a plurality of nanospecies disposed at least within the pores of the porous material, wherein the first characteristic causes the nanospecies to interact with the porous material and become disposed within the pores of the porous material.

Methods of using the structures are also provided. One exemplary method includes, among others, the following steps: contacting at least one structure with a sample and detecting at least one of the second detectable characteristics of the structure. The sample contains at least one target molecule and each structure corresponds to only one type of target molecule. When the type of target molecule is present in the sample, the structure interacts with the target molecule. Detection of each second detectable characteristic indicates the presence of the target molecule in the sample.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Figure 1A:
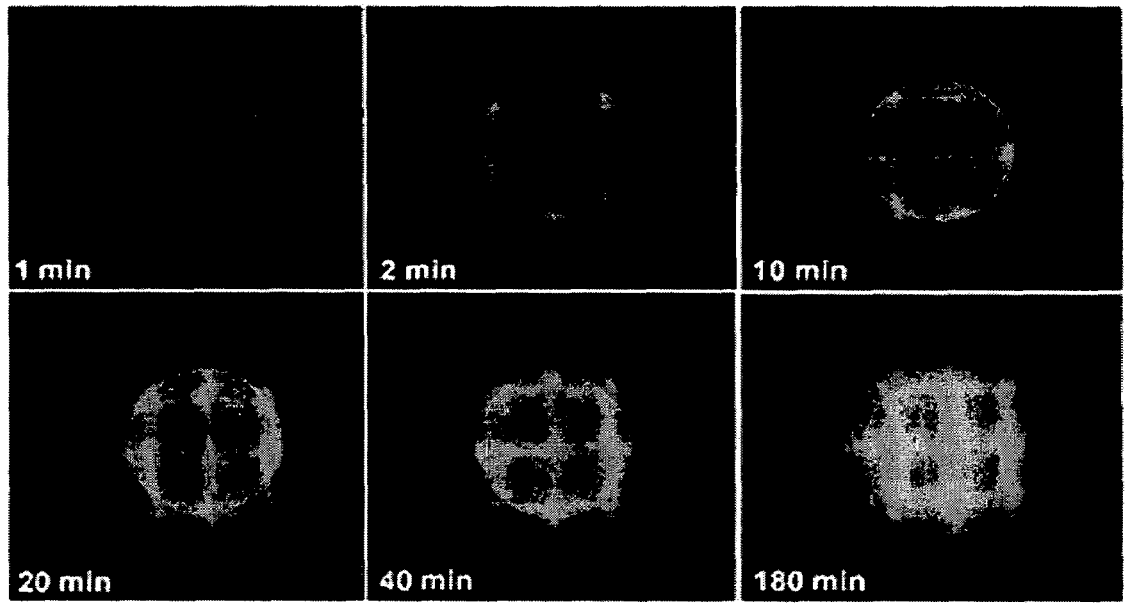
FIGS. 1A and 1B illustrates time-dependent fluorescence images showing the effects of pore size on doping kinetics (FIG. 1A, 32-nm pore beads, and FIG. 1B, 10 nm pore beads).

As embodied and broadly described herein, embodiments of the present invention, in one aspect, relate to structures having one or more classes and/or types of nanospecies disposed within the pores of a porous material, methods of fabricating these structures, and methods of using these structures. The methods of producing these structures allow for precise quantitative control of the amount of nanospecies disposed in the pores of the porous material. Therefore, if the porous material is mixed with a plurality of classes and/or types of nanospecies in appropriate ratios then many unique and distinguishable structures can be produced. In addition, since the structures are distinguishable after exposure to first energy (e.g., a light source), the structures can be individually detected based upon the production of a second detectable energy. Moreover, the structures can be modified so that the structures interact with certain target molecules, which allow detection of the target molecules after exposure to a first energy. As a result, these structures can be used as "molecular codes" to identify target molecules. The structures can be used in many fields of endeavor such as, but not limited to, biosensing, biolabeling, high-speed screening, gene expression studies, protein studies, medical diagnostics, diagnostic libraries, combinatorial libraries, microfluidic systems, optoelectronics, high-density memory, fluorescent ink (counterfeit), fluorescent cosmetics, flow cytometry, wavelength-resolved spectroscopy, multispectral imaging, fluorescent security marking, catalysis, and human identification.

As indicated hereinabove, an embodiment of the invention includes porous materials doped with one or more nanospecies. The nanospecies and the porous material have the same first characteristic. The first characteristic enhances the interaction of the nanospecies with the porous material so that the nanospecies become disposed or embedded in the pores of the porous material. This interaction allows for the precise quantitative addition of one or more type and/or classes of nanospecies to the porous material. Details regarding specific embodiments of these structures and the preparation of these structures are discussed in more detail below in Examples 1 and 2.

The first characteristic can be described as, but is not limited to, a chemical characteristic, electrical characteristic, biological characteristic, physical characteristic, or combinations thereof, that causes the nanospecies to be attracted to, bind to, or be embedded within, the porous material either directly or indirectly. For instance, the first characteristic can include, but is not limited to, a hydrophobic characteristic, a hydrophilic characteristic, an electrostatic characteristic, a biological characteristic, a bioaffinity characteristic, a ligand-receptor characteristic, an antibody-antigen characteristic, a metal chelating characteristic, a magnetic characteristic and combinations thereof. Since the porous material and nanospecies with "like" first characteristics are attracted to one another under appropriate conditions, the nanospecies can be quantitatively disposed within the pores of the porous material. For example, if the nanospecies and porous material each have a hydrophobic characteristic, then the nanospecies is attracted and binds with the porous material under appropriate conditions.

The nanospecies and/or the porous material can inherently have the first characteristic. For example, the chemical and/or biological composition of the nanospecies and/or the porous material are inherently hydrophobic, hydrophilic, etc. In addition, the nanospecies and/or the porous material can be treated, coated, or otherwise modified to have the first characteristic. For example, the nanospecies and/or the porous material can be chemically modified to be hydrophobic, hydrophilic, etc.

The porous material can include, but is not limited to, mesoporous (e.g., a pore diameter of about 1 to 100 nanometers (nm)), macroporous (e.g., a pore diameter of greater than about 100 nm), and hybrid mesoporous/macroporous materials. The shape of the porous material can be, but is not limited to, spherical, cubic, and monolith (i.e., bulk material).

The preferred shape of the porous material is spherical (e.g., a bead) having a spherical diameter of about 0.1 to 100 microns and preferably about 1 to 50 microns. The pore diameter is about 1 to 500 nm, about 5 to 200 nm, and about 10 to 50 nm. In addition, the bead can include about 500,000 to about 10 million nanospecies and more particularly, about 2 million to 6 million nanospecies within the pores of the bead. The types of beads can include, but are not limited to, silica beads and polymer beads (e.g. chromatographic beads), ceramic, and molecular sieves.

The porous material can be made of a material such as, but not limited to, a polymer, a co-polymer, a metal, a silica material, cellulose, ceramic, zeolite, and combinations thereof. The preferred porous materials are silica materials and polystyrene and polystyrene co-polymers (e.g., divinylbenzene, methacylic acid, maleic acid), which are described in more detail in Examples 1 and 2.

The classes of nanospecies can include, but are not limited to, nanoparticles (e.g., quantum dots, metal particles and magnetic particles) and biomolecules. The nanoparticle can include a number of types of nanoparticles such as, but not limited to, semiconductor, metal, and metal oxide nanoparticles (e.g., gold, silver, copper, titanium, or oxides thereof), metalloid and metalloid oxide nanoparticles, the lanthanide series metal nanoparticles, and combinations thereof. In particular, semiconductor quantum dots are described in more detail below and in U.S. Pat. No. 6,468,808 and International Patent Application WO 03/003015, which are incorporated herein by reference. Furthermore, the magnetic nanoparticles (e.g., those having magnetic properties) can include, but are not limited to, iron nanoparticles and iron composite nanoparticles. The biomolecule can include a number of types of biomolecules such as, but not limited to, polypeptides and polynucleotides. In particular, the biomolecule can include proteins, ligands, receptors, antigens, antibodies, and discrete portions thereof. Preferably, the nanospecies are semiconductor quantum dots.

The porous material can have one or more classes of nanospecies disposed therein. In addition, the porous material can have one or more different types of nanospecies within one class of nanospecies disposed therein. Moreover, one or more types of nanospecies of one or more classes of nanospecies can be disposed within a porous material.

The nanospecies can include one or more second detectable characteristics that can be used to identify the nanospecies by detecting the second detectable characteristic using appropriate detection systems. The second detectable characteristic can be caused to occur in response to exposure to a first energy such as, but not limited to, light energy, thermal energy, magnetic energy, and combinations thereof. The first energy can be produced by appropriate energy sources.

The nanospecies can include a second detectable characteristic such as, but not limited to, a fluorescent characteristic (e.g., semiconductor quantum dot), a magnetic characteristic (e.g., iron particles), a luminescent characteristic (e.g., lanthanide series metal nanoparticles), a light scattering characteristic (e.g., metal nanoparticles), a surface plasmonic characteristic (e.g., metal nanoparticles), and combinations thereof. For example, semiconductor quantum dots can be exposed to light energy and the semiconductor quantum dotes can emit fluorescent energy unique to the type of semiconductor quantum dot, as described in more detail below.

As indicated above, the nanospecies can include quantum dots such as, but not limited to, luminescent semiconductor quantum dots. In general, quantum dots include a core and a cap, however, uncapped quantum dots can be used as well. The "core" is a nanometer-sized semiconductor. While any core of the IIB-VIB, IIIB-VB or IVB-IVB semiconductors can be used in the context of the present invention, the core must be such that, upon combination with a cap, a luminescent quantum dot results. A IIB-VIB semiconductor is a compound that contains at least one element from Group IIB and at least one element from Group VIB of the periodic table, and so on. In one embodiment, the core is a IIB-VIB, IIIB-VB or IVB-IVB semiconductor that ranges in size from about 1 nm to about 20 nm. In another embodiment, the core is more preferably a IIB-VIB semiconductor and ranges in size from about 2 nm to about 10 nm. For example, the core can be CdS, CdSe, CdTe, or ZnSe.

The "cap" is a semiconductor that differs from the semiconductor of the core and binds to the core, thereby forming a surface layer on the core. The cap can be such that, upon combination with a given semiconductor core a luminescent quantum dot results. The cap should passivate the core by having a higher band gap than the core. In one embodiment, the cap is a IIB-VIB semiconductor of high band gap. For example, the cap can be ZnS or CdS. Combinations of the core and cap can include, but are not limited to, the cap is ZnS when the core is CdSe or CdS, and the cap is ZnS when the core is CdSe.

The wavelength emitted (i.e., color) by the quantum dots can be selected according to the physical properties of the quantum dots, such as the size and the material of the nanocrystal. Quantum dots are known to emit light from about 300 nanometers (nm) to 1700 nm (e.g., UV, near IR, and IR). The colors of the quantum dots include, but are not limited to, red, blue, green, and combinations thereof. The color or the fluorescence emission wavelength can be tuned continuously. The wavelength band of light emitted by the quantum dot is determined by either the size of the core or the size of the core and cap, depending on the materials which make up the core and cap. The emission wavelength band can be tuned by varying the composition and the size of the QD and/or adding one or more caps around the core in the form of concentric shells.

The intensity of the color of the quantum dots can be controlled. For each color, the use of 10 intensity levels (0, 1, 2, ... 9) gives 9 unique codes ($10^1-1$), because level "0" cannot be differentiated from the background. The number of codes increase exponentially for each intensity and each color used. For example, a three color and 10 intensity scheme yields 999 ($10^3-1$) codes, while a six color and 10 intensity scheme has a theoretical coding capacity of about 1 million ($10^6-1$). In general, n intensity levels with m colors generate (($n^m-1$) unique codes.

In general, it is more advantageous to use more colors rather than more intensity levels, in order to increase the number of usable codes. The number of intensities is preferably from 0 to 20, more preferably about 1 to 10. The number of colors is preferably about 1 to 10 (e.g., 2-8), and more preferably, about 3 to 7. By the term "multicolor quantum dot," it is meant that more than one color of luminescent quantum dots are embedded in the bead. Although preferably more than one color of quantum dots are incorporated in the bead, instances wherein one or more colors' intensity is zero, such as a bead with the red:green:blue code of 1:0:0, are also encompassed by the embodiments of the present invention.

The quantum dots can be embedded in a porous structure in a precisely controlled ratio. By the term "precisely controlled ratio," it is meant that the ratio of intensities for each color of quantum dot used is predetermined before incorporation into the porous structure. Use of quantum dots and a porous material having the same first characteristic (e.g., hydrophobic) enables the incorporation of the quantum dots into the porous material in a quantitative and precise fashion. The ordinary skilled artisan can readily determine exact ratios of quantum dots for a particular color.

The quantum dots embedded in the porous material are capable of absorbing energy from, for example, an electromagnetic radiation source (of either broad or narrow bandwidth), and are capable of emitting detectable electromagnetic radiation at a narrow wavelength band when excited. The quantum dots can emit radiation within a narrow wavelength band of about 40 nm or less, preferably about 20 nm or less, thus permitting the simultaneous use of a plurality of differently colored quantum dots disposed in the same porous material with little or no spectral overlap.

In an embodiment, the quantum dot remains embedded within the pores without the addition of a sealant. In some embodiments, the porous material can be sealed with a sealing material to protect the embedded nanospecies. In one embodiment, the sealing material should be able to substantially seal the pores in the porous material. In another embodiment, the sealing material should be able to form a layer over the outer surfaces of the porous material as well as the inner surfaces or walls of the pores without sealing the pores substantially.

The sealing materials can include, but are not limited to, polymers (e.g., polystyrene and co-polymers, amphiphilic polymers and co-polymers such as hydrocarbon (e.g., $C_2$-$C_{18}$ linear or cyclic hydrocarbons and benzene and derivatives thereof) derivatized polyacrylic acid, polymethacrylic acid, polystyrenesulfonic acid, polymaleic acid), biopolymers (e.g., proteins, polysaccharides and derivatives thereof, and lipids and derivatives thereof), surfactants, hydrogels, sol-gel compounds (e.g., mercaptopropyl-trimethoxysilane, aminopropyltrimethoxysilane, and trimethoxysilylpropymydrazide), dendrimers, polymerizable monomers and crosslinkers, and combinations thereof.

The synthesis of quantum dots is well known and is described in U.S. Pat. Nos. 5,906,670; 5,888,885; 5,229,320; 5,482,890; 6,468,808; 6,306,736; 6,225,198, etc., International Patent Application WO 03/003015, and in many research articles, all of which are incorporated herein by reference. The wavelengths emitted by quantum dots and other physical and chemical characteristics have been described in U.S. Pat. No. 6,468,808 and International Patent Application WO 03/003015 and will not be described in any further detail. In addition, methods of preparation of quantum dots is described in U.S. Pat. No. 6,468,808 and International Patent Application WO 03/003015 and will not be described any further detail.

One example of a structure includes a hydrophobic silica bead as the porous material and the hydrophobic coated quantum dot. Under appropriate conditions, the hydrophobic coated quantum dot is incorporated into the hydrophobic silica bead. In particular, the hydrophobic coated quantum dot can be coated with a chemical such as, but not limited to, an O=PR$_3$ compound, an O=PHR$_2$ compound, an O=PHR$_1$ compound, a H$_2$NR compound, a HNR$_2$ compound, a NR$_3$ compound, a HSR compound, a SR$_2$ compound, and combinations thereof. "R" can be a C$_1$ to C$_{18}$ hydrocarbon, such as but not limited to, linear hydrocarbons, branched hydrocarbons, cyclic hydrocarbons, substituted hydrocarbons (e.g., halogenated), saturated hydrocarbons, unsaturated hydrocarbons, and combinations thereof. Preferably, the hydrocarbon is a saturated linear C$_4$ to C$_{18}$ hydrocarbon, a saturated linear C$_6$ to C$_{18}$ hydrocarbon, and a saturated linear C$_{18}$ hydrocarbon. A combination of R groups can be attached to P, N, or S. In particular, the chemical can be selected from tri-octylphosphine oxide, stearic acid, and octyldecyl amine.

The hydrophobic silica bead can be formed by reacting silica beads with chemicals such as, but not limited to, a R$_n$SiCl$_{(4-n)}$ compound, a R$_n$SiO(CH$_3$)$_{(4-n)}$ compound, and a R$_n$SiO(C$_2$H$_5$)$_{(4-n)}$ compound (wherein n is 1 to 3, wherein R can be a C$_1$ to C$_{18}$ hydrocarbon, and wherein a combination of R groups can be attached to Si to form hydrophobic silica beads). The Cl, OCH$_3$ and the OC$_2$H$_5$ groups are the leaving groups during the reaction. For example, when the R$_n$SiCl$_{(4-n)}$ compound reacts with the —OH groups on the silica beads, Cl$_{(4-n)}$ combines with the H atom on the —OH group and forms a HCl leaving group, in the mean time, the R$_n$Si group attaches to the —O atom on the beads. In particular, the chemical can be selected from chloro(dimethyl)octadecylsilane, methoxy(dimethyl)octadecylsilane, (o-tolyloxy)tri(o-tolyl)silane, 3-(trimethoxysilyl)propyl methacrylate, allyldichloro(methyl)silane, butyldimethyl(dimethylamino) silane, chlorodiphenyl(diphenylmethyl)silane, chloromethyl-triethyl-silane, chlorotri(2-biphynyl)silane, chlorotri(o-tolyl)silane, chlorotri(1-naphthyl)silane, chlorotris(2-methoxyphenyl)silane, chloro(diisopropyl)silane, chloro(dimethyl)thexylsilane, chlorodimethyl(2-phenylethyl)silane, chlorodimethyl(2,3,4,5-tetramethyl-2,4-cyclopentadien-1-yl)silane, chlorotris(1,3-dimethylbutoxy) silane, diphenyl(diphenylmethoxy)(dephenylmethyl)silane, dichloro-methyl-octylsilane, dichloromethyl(2-phenethyl) silane, isobutyl(trimethoxy)silane, methyltrichlorosilane, phenyltris(2-methoxyethoxy)silane, tert-butyl-dimethyl-phenoxy-silane, trichloro(hexyl)silane, trichloro(isobutyl)silane, trichloro(octadecyl)silane, trichloro(octyl)silane, trichloro(phenethyl)silane, trichloro(phenyl)silane, triethoxy (isobutyl)silane, trichloro(vinyl)silane, trichloro(propyl)silane, triethoxy(octyl)silane, triethoxy(vinyl)silane, and trimethoxy(7-octen-1-yl)silane. Additional details regarding this example are described in Examples 1 and 2 below.

The hydrophobic silica bead including the hydrophobic coated quantum dot can be exposed to a first energy, which in response to the first energy emits fluorescent energy that can be detected.

Another example includes a polystyrene or polystyrene/divinylbenzene bead as the porous material and the hydrophobic coated quantum dot. Under appropriate conditions, the hydrophobic coated quantum dot is incorporated into the polystyrene or polystyrene/divinylbenzene bead because the polystyrene or polystyrene/divinylbenzine bead is inherently hydrophobic. Details regarding the preparation of polystryene/divinylbenzene are described in Wang, Q. C. et. al., *J. Polymer Science, Part A: Polymer Chemistry*, 32, 2577 (1994) and Kim, J. W. et. al., *Colloid Polym Sci*, 279, 146 (2001), which are incorporated herein by reference.

The polystyrene or polystyrene/divinylbenzene bead including the hydrophobic coated quantum dot can be exposed to a first energy, which in response to the first energy emits fluorescent energy that can be detected.

The structures can be prepared by mixing one or more classes and/or types of nanospecies in a solution (e.g., solvent) having the porous material disposed therein. The nanospecies are attracted to the porous material because both have the same first characteristic. In this regard, the nanospecies are attracted to the porous material and are disposed within the pores of the nanoporous material. The solution can include one or more chemical solutions that drive the nanospecies into the pores of the porous material.

For example, the hydrophobic interaction between hydrophobic quantum dots and a hydrophobic bead having a hydrocarbon coating is stronger than salvation (i.e., interaction of hydrocarbon and quantum dots with the solvents). The chemical solution can be a mixture of alcohol and chloroform for hydrophobic quantum dot incorporation.

In other embodiments, the solution for hydrophobic quantum dot incorporation can also include, but is not limited to, chemical organic solvents, such as acyl, aliphatic, cycloaliphatic, aromatic or heterocyclic hydrocarbons or alcohols with or without halogens, oxygen, sulfur, and nitrogen, although in some instances, water or aqueous solutions can be used. Examples of useful solvents include, but are not limited to, benzene, toluene, xylene, cyclohexane, pentane, hexane, ligroin, methyl isobutyl ketone, methylacetate, ethylacetate, butylacetate, methyl CELLOSOLVE® (Union Carbide), ethyl CELLOSOLVE® (Union Carbide), butyl CELLOSOLVE® (Union Carbide), diethylene glycol monobutyl ether, diethylene glycol monobutyl ether acetate, alcohol (e.g., methanol, ethanol, n-propanol, i-propanol, n-butanol, t-butanol, n-pentanol, n-hexanol, branched hexanol, cyclohexanol, 2-ethylhexyl alcohol), acetone, DMSO, methylene chloride, chloroform, and combinations thereof. In one embodiment, the solvent is alcohol, and more preferably it is a C$_3$-C$_6$ linear or branched alcohol. In another embodiment, the solvent is butanol (normal or tertiary), and the bead is a cross-linked polymer derived from styrene/divinylbenzene/acrylic acid.

The type of solution depends upon, at least in part, the first characteristic of the nanospecies and the porous material. As mentioned above, the first characteristic can be a chemical characteristic, an electrical characteristic, a biological characteristic, a physical characteristic, or combinations thereof. In particular, the first characteristic can include a hydrophobic characteristic, a hydrophilic characteristic, an electrostatic characteristic, a biological characteristic, a bioaffinity characteristic, a ligand-receptor characteristic, an antibody-antigen characteristic, a metal chelating characteristic, magnetic characteristic and combinations thereof. In general, the porous material (e.g., beads) and the nanospecies should be able to suspend or immerse in the selected solution. For example, quantum dot encoded silica beads, the quantum dots and the silica beads can be suspended in an alcohol and chloroform mixture. In another example, if the nanospecies and the porous material are hydrophilic, a polar solvent solution can be selected to dissolve or suspend the nanospecies with the porous material. In an additional example, if the porous material is coated with antigens and the nanospecies are antibodies, the antibodies and the antigen coated porous material should be suspended in an aqueous solution to avoid denature of the biomolecules.

Additional methods for fabricating the structure are described in U.S. Pat. No. 6,468,808 and International Patent Application WO 03/003015.

In another embodiment, a conjugate that includes a substrate (e.g., porous material having nanospecies disposed therein) and a probe attached to the porous material is provided. The probe can be a chemical molecule or biomolecule capable of being linked to the porous material either directly or indirectly via a linker. In addition, the probe has an affinity for one or more target molecules for which detection is desired. If, for example, the target is a nucleic acid sequence, the probes should be chosen so as to be substantially complementary to a target molecule sequence, such that the hybridization of the target and the probe occurs. The term "substantially complementary" means that the probes are sufficiently complementary to the target sequences to hybridize under the selected reaction conditions.

The probe can be selected from, but is not limited to, polypeptides (e.g., protein such as, but not limited to an antibody (monoclonal or polyclonal)), nucleic acids (both monomeric and oligomeric), polysaccharides, sugars, fatty acids, steroids, purines, pyrimidines, drugs, or ligands. Lists of suitable probes are available in "Handbook of Fluorescent Probes and Research Chemicals", (sixth edition), R P. Haugland, Molecular Probes, Inc., which is incorporated in its entirety herein by reference.

Use of the phrase "polypeptide" or "protein" is intended to encompass a protein, a glycoprotein, a polypeptide, a peptide, and the like, whether isolated from nature, of viral, bacterial, plant, or animal (e.g., mammalian, such as human) origin, or synthetic, and fragments thereof. A preferred protein or fragment thereof includes, but is not limited to, an antigen, an epitope of an antigen, an antibody, or an antigenically reactive fragment of an antibody.

Use of the phrase "nucleic acid" is intended to encompass DNA and RNA, whether isolated from nature, of viral, bacterial, plant or animal (e.g., mammalian, such as human) origin, synthetic, single-stranded, double-stranded, comprising naturally or non-naturally occurring nucleotides, or chemically modified.

The probe can be attached to the porous material directly or indirectly by stable physical, chemical, or biological associations. For example, the probe can be attached to the porous material directly or indirectly through one or more covalent bonds. Direct linking of the probe and the porous material implies only the functional groups on the porous material surface and the probe itself serve as the points of chemical and/or attachment. If the probe is attached to the porous material indirectly, the attachment is by means of a "linker," intermediate cross-linker, or a bi-functional compound. In addition, when the porous material has a sealing layer disposed thereon, the probe can be attached to the sealing material.

Use of the term "linker" is intended to encompass, but is not limited to, mono- or bifunctional physical, chemical, or biological associations that can be used to link the probe to the porous material. For example, the linker can include compounds having one or more amine, carboxylic, hydroxy, and/or thiol groups. Exemplary biological linkers can include streptavidin, neutravidin, avidin and biotin. More than one linker can be used to attach a probe such as in a daisy chain manner (e.g., porous material-linker1-linker2-linker3-probe). In addition, one linker can be attached to the porous material (e.g., biotin) and one linker can be attached to the probe (e.g., avidin). In general, the linker should not contact the protein probe or a fragment thereof at an amino acid essential to the function, binding affinity, or activity of the attached protein.

In one embodiment, the surface of the porous material can be surface-modified by functional organic molecules with reactive groups such as thiols, amines, carboxyls, and hydroxyl to interact with the probes. These surface-active reactants include, but are not limited to, aliphatic and aromatic amines, mercaptocarboxylic acid, carboxylic acids, aldehydes, amides, chloromethyl groups, hydrazide, hydroxyl groups, sulfonates, and sulfates.

A plurality of probes of the same type can be attached to a porous material. In addition, a plurality of different types of probes can be attached to the porous material to allow for the simultaneous detection of multiple targets. In general, up to about 100,000,000 probes can be attached to a porous material such as a bead, while even more probes can be attached to bulk monolith porous materials. The attachment of the probe to the substrate can occur through, for example, covalent bonding, ionic bonding, hydrogen bonding, van der Waals forces, and mechanical bonding.

The present invention also provides a method of making the conjugate. Where the probe is to be directly attached to the substrate, the method includes (a) attaching the probe to the substrate; and (b) isolating the conjugate. In another embodiment, the method of making the conjugate includes the steps of (a) contacting a probe with (i) one or more linkers, and (ii) the substrate; and (b) isolating the conjugate. In still another embodiment, the method of making the conjugate includes the steps of (a) attaching a linker to the substrate; (b) attaching the probe to the linker; and (c) isolating the conjugate.

In an embodiment where the pores of the porous material are sealed, the probe is attached to the outer surface of the porous material either directly or indirectly. In another embodiment where the pores are not sealed (e.g., where the pores are of a sufficient diameter that the sealing material coats the inside of the pore walls without sealing the pores closed), the probes can be attached to the outside of the porous material as well as the inside walls of the pores.

One or more conjugates can be used in the detection of one or more target molecules. Each type of conjugate can be fabricated to have a unique and distinguishable code, which enables the simultaneous detection of multiple target molecules. In addition, the target molecules may include a chemical (e.g., fluorochrome) or structure having a detectable characteristic (e.g., fluorescence) to indicate that the target molecule is bound to the conjugate. Thus, when the conjugate having a target molecule is exposed to a first energy, the nanospecies can emit a second detectable energy and the target molecule can emit a third detectable energy. Therefore, detection of both the second energy and the third energy indicate that the target molecule is disposed on the conjugate.

Conjugates can be used in areas such as, but not limited to, biosensing, biolabeling, high-speed screening, gene expression studies, protein studies, medical diagnostics, diagnostic libraries, combinatorial libraries, microfluidics, flow cytometry, and spectroscopy, and imaging. In addition, the conjugates can be used as, but are not limited to, contrast agents (e.g., for animal experiments and molecular probes) and microcarriers (e.g., drug delivery). Furthermore, the conjugate can be used to label cells, tissues, or microplates, for example. In particular, the conjugate can be used in molecular beacons.

The detection of the conjugates can be performed using detection systems in the art for the particular experimental technique being used. For example, the detection system can be a detection system that detects fluorescence.

The target molecule can include chemical compounds (e.g., organic or inorganic) or biological compounds having an affinity for the probe. The biological compound can include biomolecules, such as, but not limited to, proteins, nucleic acids, nucleotides, oligonucleotides, antigens, antibodies, ligands, portions of a gene, regulatory sequences, genomic DNA, cDNA, and RNA including mRNA and rRNA. In addition, the target molecule can be included in solutions, cells, or tissues.

In general, the conjugate can be used to detect one or more targets in a sample by (a) contacting the sample with one or more conjugates, wherein the probes of one or more of the conjugates specifically binds to one or more of the target molecules; and (b) detecting the presence of the conjugate. By "specifically binds," it is meant that the probe preferentially binds the target molecule with greater affinity than non-targeted molecules in the sample.

In addition, two or more regions on a given target molecule can be simultaneously detected in a sample. For example, a method of detecting two or more regions of a single target molecule involves using a set of conjugates, wherein each of the conjugates, having a unique and distinguishable nanospecies, is attached to a probe that specifically binds to a different region on a given target molecule in the sample. Detection of the different regions on the target molecule arises from the unique code generated by the different conjugates. In particular, this method enables different functional domains of a single protein to be distinguished. In addition, a single conjugate with different probes attached to it can be used simultaneously to detect two or more different target molecules and/or two or more regions on a target molecule.

Use of one or more conjugates allows for the detection of multiple target molecules (or multiple portions of a target molecules), which facilitates the use of the conjugates in biosensing, biolabeling, high-speed screening, gene expression studies, protein studies, medical diagnostics, diagnostic libraries, combinatorial libraries, microfluidics, flow cytometry, spectroscopy, and imaging, as mentioned above.

In one embodiment, a flow cytometer can be used in multiplexed assay procedures for detecting one or more target molecules using one or more conjugates. Flow cytometry is an optical technique that analyzes particular particles (e.g., beads) in a fluid mixture based on the particles' optical characteristics. Flow cytometers hydrodynamically focus a fluid suspension of particles into a thin stream so that the particles flow down the stream in substantially single file and pass through an examination zone. A focused light beam, such as a laser beam, illuminates the particles as they flow through the examination zone. Optical detectors within the flow cytometer measure certain characteristics of the light as it interacts with the particles. Commonly used flow cytometers can measure particle fluorescence at one or more wavelengths.

One or more target molecules can be detected using a conjugate (e.g., a structure such as a quantum dot-tagged bead), one or more probe having an affinity for one or more of the target molecules, and a fluorophore attached to the target molecules. Prior to being introduced to the flow cytometer, the conjugates specific for certain target molecules are mixed with a sample that may include one or more target molecules. The conjugates interact with (e.g., bond or hybridize) the corresponding target molecules for which the probe has an affinity. Subsequently, the conjugate is removed and mixed with fluorophores, so that the target molecules attach to the fluorophores. Alternatively, the fluorophores can be attached to the target molecules before being introduced to the conjugates.

Next, the conjugates are introduced to the flow cytometer. As discussed above, the flow cytometer is capable of detecting the conjugates and the fluorophore after exposure to a first energy. Detection of the fluorophore indicates that a target molecule is present in the sample. Detection of the conjugate associated with the detection of the fluorophore indicates the identity of the target molecule detected, since the probe on the conjugate has a specific affinity for a particular target molecule.

In another embodiment, molecular beacons can be used to detect one or more polynucleotides. A molecular beacon includes a conjugate (e.g., a structure such as a quantum dot-tagged bead), a probe, a fluorophore, and a quenching moiety. The probe is a single-stranded oligonucleotide comprising a stem and loop structure wherein a hydrophilic attachment group is attached to one end of the single-stranded oligonucleotide and the quenching moiety is attached to the other end of the single-stranded oligonucleotide. The fluorophore can be any fluorescent organic dye or a single quantum dot such that its emission does not overlap with that of the quantum dot-tagged bead. The quenching moiety desirably quenches the luminescence of the fluorophore. Any suitable quenching moiety that quenches the luminescence of the fluorophore can be used in the conjugate described above.

The loop of the oligonucleotide includes a probe sequence that is complementary to a target sequence in the polynucleotide to be detected in the sample. Desirably, the loop is of sufficient size such that it opens readily upon contact with a target sequence, yet not so large that it is easily sheared. The stem is formed by the annealing of complementary sequences that are at or near the two ends of the single-stranded oligonucleotide. A fluorophore is linked to one end of the single-stranded oligonucleotide and a quenching moiety is covalently linked to the other end of the single-stranded oligonucleotide. The quantum dot-tagged bead can be then attached (either directly or indirectly) to either the fluorophore or the quenching moiety. The stem keeps the fluorophore and quenching moieties in close proximity to each other so that the luminescence of the fluorophore is quenched when the single-stranded oligonucleotide is not bound to a target sequence. In this regard, the complementary sequences of which the stem includes should be sufficiently close to the ends of the oligonucleotide as to effect quenching of the quantum dots.

When the probe sequence encounters a target sequence in a polynucleotide to be detected in a sample, it binds (i.e., hybridizes) to the target sequence, thereby forming a probe-target hybrid that is longer and more stable than the stem hybrid. The length and rigidity of the probe-target hybrid prevents the simultaneous formation of the stem hybrid. As a result, the structure undergoes a spontaneous conformational change that forces the stem to open thereby separating the fluorophore and the quenching moiety and restoring luminescence of the fluorophore. The luminescence of the fluorophore indicates that the target molecule is bound to the probe, and the emission code of the quantum dot-tagged bead identifies the probe and hence the target. The target itself does not have to be fluorescently labeled when using this type of molecular beacon.

Additional details regarding methods and techniques that use quantum dots for detecting biomolecules has been described in U.S. Pat. No. 6,468,808 and International Patent Application WO 03/003015.

Now having described the embodiments of the structure in general, Example 1 describes some embodiments where the porous material is a silica bead having quantum dot nanospecies disposed therein, while Example 2 describes some embodiments where the porous material is a polystyrene bead having quantum dot nanospecies disposed therein. While embodiments of structures having nanospecies disposed in the porous material are described in connection with Examples 1 and 2, and the corresponding text and figures, there is no intent to limit embodiments of the structures to these descriptions. On the contrary, the intent is to cover all alternatives, modifications, and equivalents included within the spirit and scope of embodiments of the present invention.

EXAMPLE 1

True-color fluorescence images of mesoporous silica beads (about a 5-μm diameter, about a 32 nm pore size) doped with single-color quantum dots emitting light at about 488 nm (blue), about 520 nm (green), about 550 nm (yellow), about 580 nm (orange), or about 610 nm (red) have been produced. These beads are considered "monochromatic" because they were prepared by using single-color quantum dots, and were mixed and spread on a glass surface for fluorescence imaging. Although only a single light source (a near-UV lamp) was used for excitation, all the doped beads were observed and were clearly distinguishable. It is worth noting that simultaneous excitation of multiple emission colors is a unique property of quantum dots, and is not possible with organic dyes or lanthanide compounds. The quantum dot-doped beads are remarkably bright, and can be recorded by using a digital color camera and a mercury lamp. Quantitative measurements indicate that these mesoporous beads are about 50-100 times brighter than the quantum dot-tagged latex beads reported previously, and are more than 30 times brighter than nonporous polystyrene beads of similar sizes.

One factor contributing to the improved brightness is the large surface area (150 ra$^2$ per gram for the 32-nm pore beads), about 50-100 times larger than the surface area of nonporous beads. Also, the quantum dots are able to penetrate deeply into the mesoporous beads, as shown by the remarkably uniform fluorescence across the bead ulterior. In comparison, the penetration depths of quantum dots into polystyrene beads do not exceed 5% of the bead's radius as measured by transmission electron microscopy, even under extensive swelling conditions. Confocal fluorescence imaging shows a clear ring pattern confirming that the quantum dots are primarily located on the surface or the adjacent layer (data not shown). This is not surprising because previous research has shown that even hydrogels such as Sepharose do not allow penetration of 30-nm colloidal gold beyond a 0.1-0.2 (nm boundary layer.

Figure 1B:
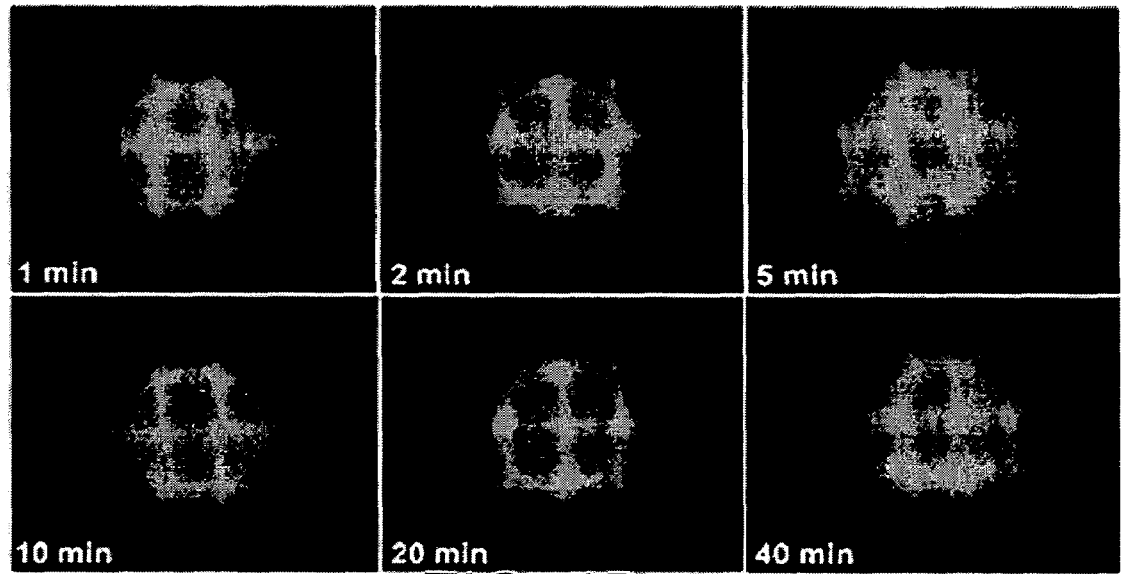

FIGS. 1A and 1B illustrate time-dependent fluorescence images showing the effects of pore size on doping kinetics (FIG. 1A, 32-nm pore beads, and FIG. 1B, 10-nm pore beads). Except the pore size, all other bead properties (e.g., size, material, and surface chemistry) and the data acquisition conditions (e.g., excitation wavelength, intensity, and exposure time) were the same. The effect of pore size on doping kinetics is examined by comparing the time-dependent fluorescence signals for two types of silica beads, one with a pore size of 32 nm and the other 10 nm. The results reveal that doping is remarkably fast for the 32 nm pore beads, achieving nearly uniform quantum dot distribution in one minute and saturation in less than 5 minutes. For the 10 nm pore beads, however, a blurred ring structure is observed for doping from about 1 to 60 minutes, indicating that doping primarily occurs on the bead surface. This uneven structure disappears after about 3 hours, but the fluorescence intensity is not saturated until about 10 hours later. This comparison suggests that the 32 nm pores are large enough for rapid quantum dot diffusion, but the 10 nm pores significantly reduce quantum dot diffusion and the doping kinetics. Considering the thickness of the hydrocarbon coating (2 nm on all sides), the open space in a 10 nm pore would be reduced to 6 nm, roughly the dimension of a 3-4 nm quantum dot plus a 1-nm TOPO capping layer. Doping can still occur because both the hydrocarbon and the surfactant molecules are conformationally flexible and can insert into each other in a stable, interdigitated configuration.

Figure 2A:
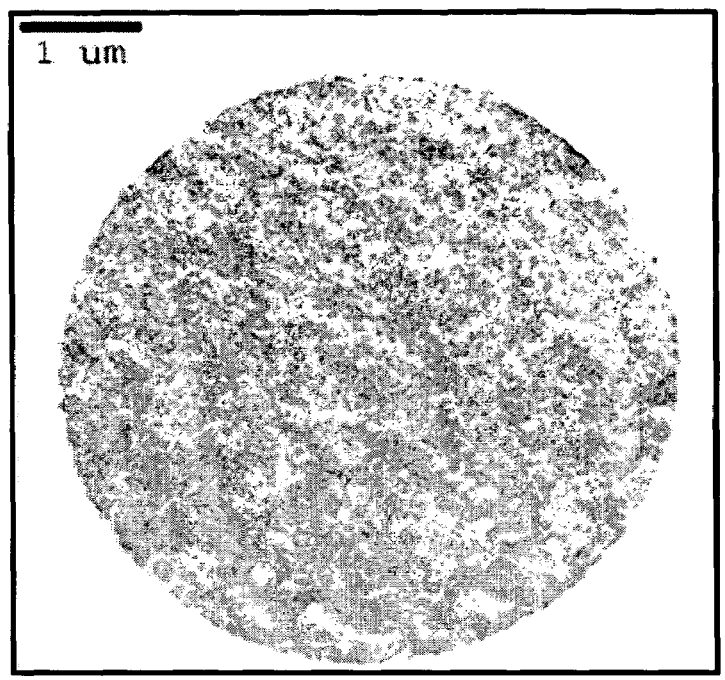
FIG. 2A illustrates TEM images of a 5 µm silica bead showing the highly porous internal structure.
Figure 2B:
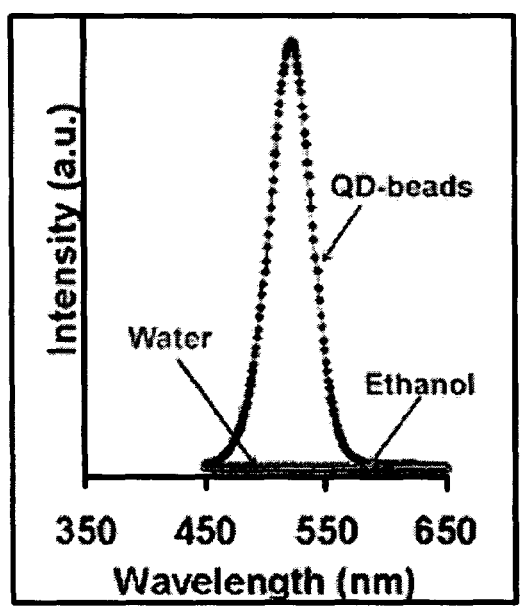
FIG. 2B illustrates fluorescence data showing the stability of the doped beads and the absence of quantum dots leaching into water or ethanol after overnight exposure at room temperature.
Figure 2C:
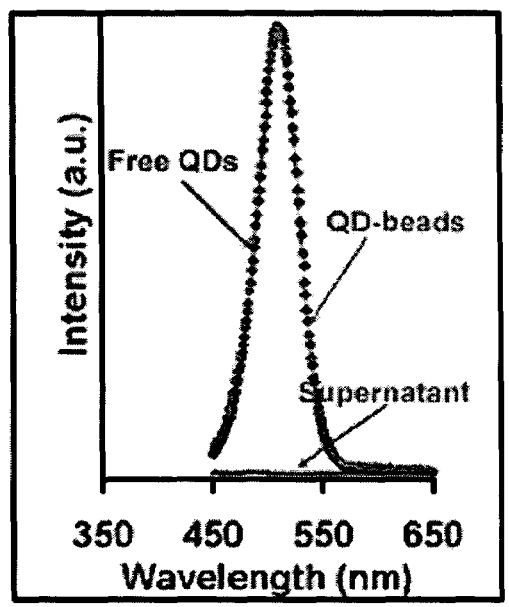
FIG. 2C illustrates fluorescence data showing identical optical properties of quantum dots dispersed in solution or immobilized in mesoporous silica beads.

FIG. 2A illustrates TEM images of a 5 mm silica bead showing the highly porous internal structure. FIG. 2B illustrates fluorescence data showing the stability of the doped beads and the absence of quantum dots leaching into water or ethanol after overnight exposure at room temperature. FIG. 2C illustrates fluorescence data showing identical optical properties of quantum dots dispersed in solution or immobilized in mesoporous silica beads. The supernatant curve showed no quantum dots in the solution (100% incorporation into the beads). TEM measurement of the doped beads (prepared as thin sections) confirmed the highly porous structure, but could not resolve single nanopores or quantum dots at relatively low resolutions. Inside the pores, quantum dots are confined via hydrophobic interactions between the hydrocarbon and TOPO molecules. Assuming a surface density of 1-2 hydrocarbon or TOPO molecules per square nanometer (typical for monolayer coverage), it is estimated that about 10 TOPO molecules on a single dot can react with roughly the same number of hydrocarbon molecules on the nanopore wall (based on a sterically allowed solid angle of 0.5 n for molecular interactions). As widely known in chemistry and biology, weak multivalent interactions can lead to stable complexes with very slow dissociation rates. Thus, the quantum dots are expected to be firmly immobilized in the pores and are stable against dissociation or leaching. FIG. 2B illustrates that no QD leakage was observed when the doped beads were exposed overnight to water or common organic solvents (e.g., ethanol, acetone, acetonitrile, and DMF).

FIG. 2C illustrates that the optical properties of quantum dots are nearly identical, either when they are dispersed in organic solvents or are immobilized in silica beads. This indicates that the QDs are spatially isolated from each other inside the beads, similar to that of organic dyes dispersed in mesoporous silica. By using two independent measures (single-dot spectroscopy and bulk concentration measurement) reported previously, it can be estimated that the numbers of quantum dots per bead are as large as 2-6 million (depending on the pore size), corresponding to about 5% surface coverage or occupancy rate. This condition is far from surface saturation and is favorable for quantum-dot dispersion inside the beads. Quantitative data further reveal that essentially no quantum dots are left in the free solution due to nearly 100% quantum dot incorporation into the beads. This is especially important for multicolor doping, in which the amounts of different quantum dots must be controlled precisely.

Figure 3:
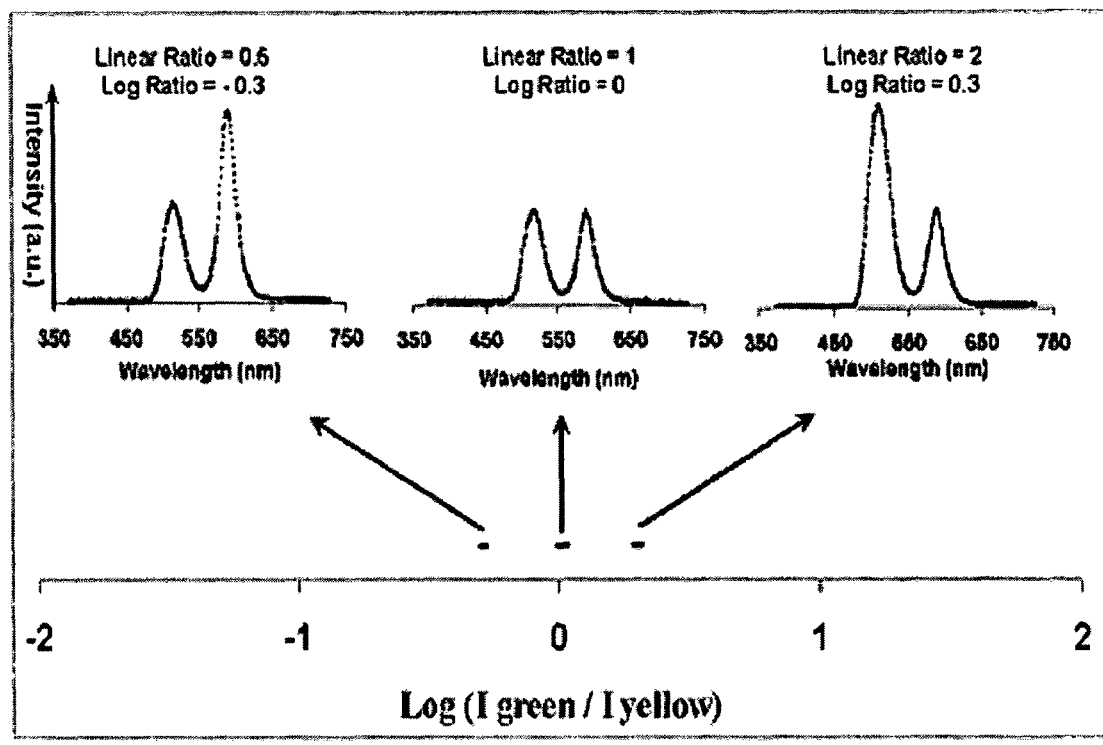
FIG. 3 illustrates ratiometric doping results using two QD colors and two intensity levels.

FIG. 3 illustrates ratiometric doping results using two quantum dot colors and two intensity levels. The top portion of FIG. 3 illustrates the actual fluorescence spectra showing three intensity ratios of 3:2, 1:1, and 2:1 at emission wavelengths of 510 and 580 nm, while the bottom portion illustrates a scatter plot of the intensity ratios (log scale) based on 30 data points (single-bead measurements) for each ratio. Using two intensities, there are three unique intensity ratios (1:2, 1:1, and 2:1). These ratios are remarkably robust in a given class of doped beads, although the absolute intensities could vary considerably from bead to bead (due to variations in bead size and instrumental alignment). As can be seen from the tight scatter plot, the standard deviations for these intensity ratios are less than 2.0%. This high level of reproducibility allows 20 intensity ratios to be distinguished within one log along the x-axis, and 40 ratios within two logs. Thus, in a 3-color doping scheme (yielding two independent ratios), 400 doping combinations are possible with ±1 log, and up to 1,600 combinations are possible with +2 logs. As reported by Weiss and coworkers for biomolecular imaging, ratiometric measurements are much more reliable than absolute intensities because the ratio values are not affected by simultaneous drifts or fluctuations of the individual signals. This advantage will help the development of microdevices and algorithms for reading the doped beads at high accuracies and speeds.

In comparison with other doping or optical encoding technologies, the use of mesostructured silica provides an unprecedented level of doping control, better than 2% reproducibility, and low production costs. For potential applications in combinatorial or multiplexed assays, the doped beads can be linked to biomolecules such as oligonucleotides, peptides, or antibodies. Both the outer bead surface and the internal pore surface might be used because the mesoporous structure allows rapid diffusion and fast response. In addition, quantum dot-doped mesoporous fibers and thin films will have applications in chemical/biological sensing, quantum-dot lasers, and integrated optoelectronics. Furthermore, the multivalent doping method can be extended to electrostatic, ligand-receptor, and metal ion chelating interactions for doping nanoporous materials with various molecules and nanoparticles.

Materials: Core-shell quantum dots (ZnS-capped CdSe) were synthesized according to literature procedures. The resulting quantum dots were coated with a layer of tri-n-octylphosphine oxide (TOPO), which was used as a high-temperature coordinating solvent. The quantum dot's fluorescence quantum yields were about 50% at room temperature, with size variations of about 5%. Mesoporous materials were synthesized by using pore-generating templates such as self-assembled surfactants or polymers (called porogens). After synthesis, removal of the templates generated mesosized pores, which were either ordered or random depending on the template structures. In this work, mesoporous silica beads (about 5 μm diameter) with pore sizes of about 10 nm or 32 nm were obtained from Phenomenex (Torrance, Calif.). The pore surfaces were coated with a monolayer of Si—$C_{18}H_{37}$ (octadecyl or C18, an 18-carbon linear-chain hydrocarbon).

These silica materials contained random pores, but the basic principles and methods should be applicable to ordered pores as well.

Doping: Single-color doping was accomplished by mixing porous beads with a controlled amount of quantum dots in an organic solvent (butanol). For the 32-nm pore beads, the doping process was complete in less than 10 minutes (no free dots left in solution). For the 10-nm pore beads, more extended times were used to study the doping kinetics. For multi-color doping, different-colored quantum dots were pre-mixed in precisely controlled ratios. Porous beads were added to an aliquat of this pre-mix solution. Doped beads were isolated by centrifugation, and washed three times with ethanol.

Transmission Electron Microscopy (TEM): The doped beads were embedded in a resin (Ted Pella, Redding, Calif.), and were cut into 60-70 nm thin sections on an ultramicrotome machine (Leica Ultracut S, Bannockburn, L). The thin sections were imaged on a Hitachi H about 7500 transmission electron microscope operating at 75 k voltage with a magnification of 23,000.

Optical Imaging and Spectroscopy: True-color fluorescence imaging was achieved with an inverted Olympus microscope (IX-70) equipped with a digital color camera (Nikon Dl), a broad-band ultraviolet (330-385 nm) light source (100-W mercury lamp), and a longpass interference filter (DM 400, Chroma Tech, Brattleboro, Vt.). Wavelength-resolved spectra were obtained by using a single-stage spectrometer (SpectraPro 150, Roper Scientific, Trenton, N.J.).

EXAMPLE 2

True-color fluorescence images of doped with single-color quantum dots (about a 15-μm diameter) doped with single-color quantum dots emitting light at about 488 nm (blue), about 520 nm (green), about 550 nm (yellow), about 580 nm (orange), or about 610 nm (red) have been produced. These beads are considered "monochromatic" because they were prepared by using single-color quantum dots, and were mixed and spread on a glass surface for fluorescence imaging. Although only a single light source (a near-UV lamp) was used for excitation, all the doped beads were observed and were clearly distinguishable. It is worth noting that simultaneous excitation of multiple emission colors is a unique property of quantum dots, and is not possible with organic dyes or lanthanide compounds. The quantum dot-doped beads are remarkably bright, and can be recorded by using a digital color camera and a mercury lamp.

Figure 4:
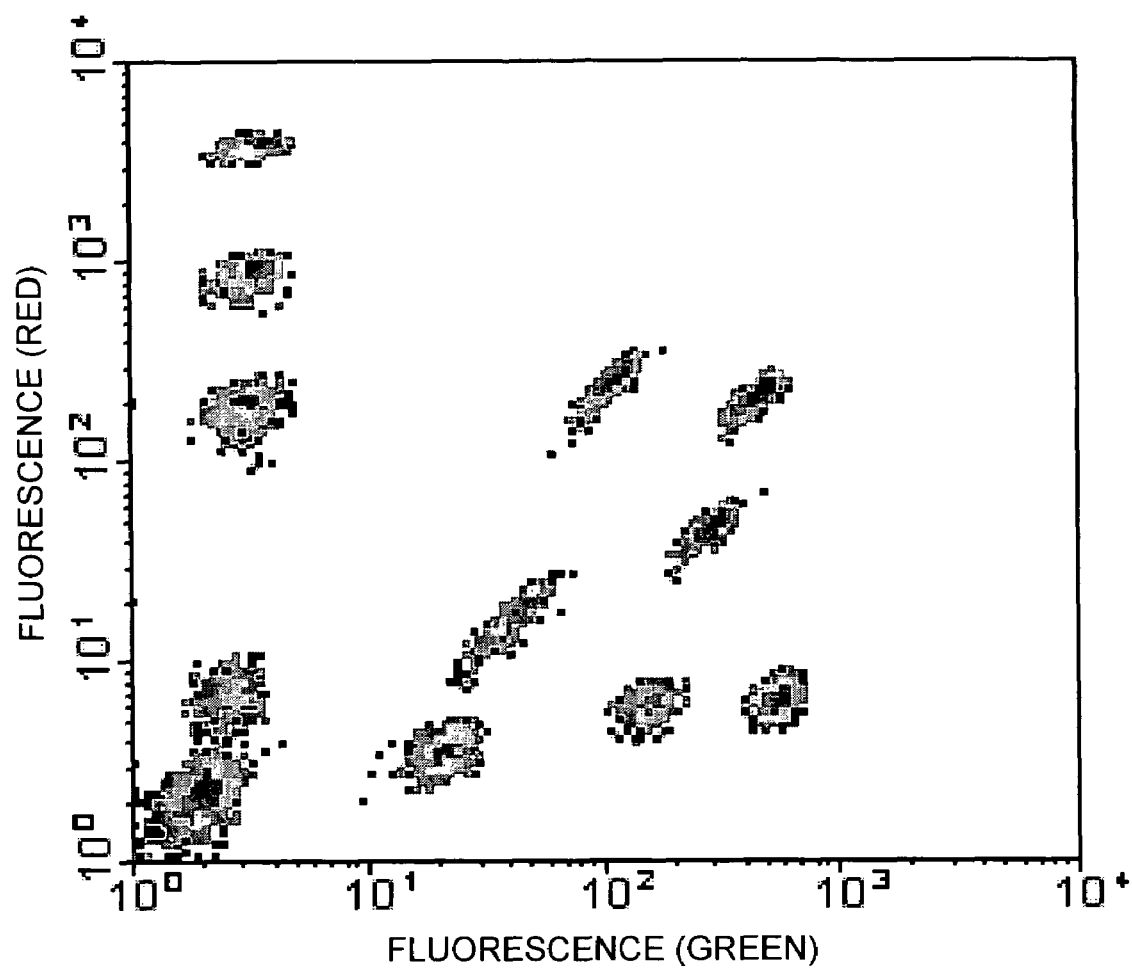
FIG. 4 illustrates a two-dimensional density plot showing classification of a number of microsphere sets based on simultaneous analysis of green fluorescence and red fluorescence.

FIG. 4 illustrates a two-dimensional density plot showing classification of the twelve microsphere sets (including control, blank microsphere) based on simultaneous analysis of green fluorescence and red fluorescence. This graph illustrates that flow cytometry can be used to decode a set of multicolor quantum dot encoded polystyrene beads.

Materials: Core-shell quantum dots (ZnS-capped CdSe) were synthesized according to literature procedures. The resulting quantum dots were coated with a layer of tri-n-octylphosphine oxide (TOPO), which was used as a high-temperature coordinating solvent. The quantum dot's fluorescence quantum yields were about 50% at room temperature, with a size variation of about 5%. Mesoporous polystyrene materials were synthesized according to procedures.

Doping: Single-color doping was accomplished by mixing porous beads with a controlled amount of quantum dots in an organic solvent such as butanol. For multi-color doping, different-colored quantum dots were pre-mixed in precisely controlled ratios. Porous beads were mixed with an aliquot of this pre-mix solution. Doped beads were isolated by centrifugation, and washed three times with ethanol.

Optical Imaging and Spectroscopy: True-color fluorescence imaging was achieved with an inverted Olympus microscope (IX-70) equipped with a digital color camera (Nikon Dl), a broad-band ultraviolet (330-385 nm) light source (100-W mercury lamp), and a long-pass interference filter (DM 400, Chroma Tech, Brattleboro, Vt.). Wavelength-resolved spectra were obtained by using a single-stage spectrometer (SpectraPro 150, Roper Scientific, Trenton, N.J.).

Flow cytometry. The quantum dot encoded microbeads can be decoded with virtually any commercially available flow-cytometer. In this experiment, the beads were analyzed with FlowScan and FlowSort (Becton Dickinson).

It should be emphasized that the above-described embodiments of the present invention, particularly, any "preferred" embodiments, are merely possible examples of implementations, and are merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

Therefore, having thus described the invention, at least the following is claimed:

1. A structure, comprising:
a first structure embedded within pores of a second structure,
wherein the first structure includes a quantum dot having a first characteristic, wherein a detectable luminescent optical signature is produced by the quantum dot upon exposure to a first energy; and
wherein the second structure includes a porous material having the first characteristic and a plurality of pores, wherein the first characteristic of the quantum dot and the first characteristic of the porous material are the same, where an interaction of the first characteristic of the quantum dot with the first characteristic of the porous material cause the quantum dot to interact with the porous material and become embedded within the pores of the porous material, wherein the quantum dot remains embedded within the pores without the addition of a sealant, and wherein the first characteristic is selected from a hydrophobic characteristic, a hydrophilic characteristic, an electrostatic characteristic, and combinations thereof.

2. The structure of claim 1, wherein the porous material is selected from a mesoporous material, a macroporous material, and a hybrid mesoporous/macroporous material.

3. The structure of claim 1, wherein the porous material is made of a material selected from a polymer, a metal, a silica material, cellulose, ceramic, zeolite, and combinations thereof.

4. The structure of claim 1, wherein the porous material is silica having a hydrocarbon-derivatized surface.

5. The structure of claim 1, wherein the quantum dot is a hydrophobic coated semiconductor quantum dot, wherein the coating includes a hydrophobic compound substantially disposed on the semiconductor quantum dot.

6. The structure of claim 5, wherein the hydrophobic compound is selected from a $O\!=\!PR_3$ compound, an $O\!=\!PHR_2$ compound, an $O\!=\!PHR_1$ compound, a $H_2NR$ compound, a $HNR_2$ compound, a $NR_3$ compound, a $HSR$ compound, a $SR_2$ compound, and combinations thereof, wherein R is selected from $C_1$ to $C_{18}$ hydrocarbons, and combinations thereof.

7. The structure of claim 6, wherein R is a saturated linear $C_4$ to $C_{18}$ hydrocarbon.

8. The structure of claim 5, wherein the hydrophobic compound is selected from an $O\!=\!PR_3$ compound, a $HNR_2$ compound, a $HSR$ compound, a $SR_2$ compound, and combinations thereof.

9. The structure of claim 5, wherein the hydrophobic compound is selected from tri-n-octylphosphine, stearic acid, and octyldecyl amine.

10. The structure of claim 5, wherein the hydrophobic compound includes tri-n-octylphosphine.

11. The structure of claim 5, wherein the hydrophobic compound includes stearic acid.

12. The structure of claim 5, wherein the hydrophobic compound includes octyldecyl amine.

13. The structure of claim 5, wherein the quantum dot comprises a core and a cap.

14. The structure of claim 5, wherein the core of the quantum dot is selected from the group consisting of IIB-VIB semiconductors, IIIB-VB semiconductors, and IVB-IVB semiconductors.

15. The structure of claim 14, wherein the core of the quantum dot is selected from the group consisting of IIB-VIB semiconductors.

16. The structure of claim 14, wherein the core of the quantum dot is CdS or CdSe.

17. The structure of claim 14, wherein the cap is selected from the group consisting of IIB-VIB semiconductors of high band gap.

18. The structure of claim 14, wherein the cap is selected from ZnS and CdS.

19. The structure of claim 1, further comprising a probe attached directly to the porous material.

20. The structure of claim 1, further comprising a probe attached indirectly to the porous material via a linking compound.

21. The structure of claim 20, where the probe is selected from a biomolecule and a biomolecule attached to a fluorophore.

22. The structure of claim 21, where the probe is selected from a biomolecule and a biomolecule attached to a fluorophore.

23. The structure of claim 1, further comprising a probe, attached to the porous material, and a fluorophore and a quenching moiety attached to the probe.

24. The structure of claim 1, wherein the pores have a diameter from about 10 to about 50 nanometers.

25. The structure of claim 1, wherein the first structure is nonporous.

* * * * *

UNITED STATES PATENT AND TRADEMARK OFFICE
CERTIFICATE OF CORRECTION

PATENT NO. : 7,648,845 B2  Page 1 of 1
APPLICATION NO. : 11/385504
DATED : January 19, 2010
INVENTOR(S) : Nie et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 435 days.

Signed and Sealed this

Twenty-third Day of November, 2010

David J. Kappos
*Director of the United States Patent and Trademark Office*